US009196082B2

(12) United States Patent
Pearlstein et al.

(10) Patent No.: US 9,196,082 B2
(45) Date of Patent: *Nov. 24, 2015

(54) SYSTEMS AND METHODS FOR CHARACTERIZING SPATIAL DISTORTION IN 3D IMAGING SYSTEMS

(71) Applicant: Loma Linda University Medical Center, Loma Linda, CA (US)

(72) Inventors: Robert D. Pearlstein, Durham, NC (US); David Scott Kittle, Durham, NC (US); Barbara Ann Holshouser, Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/267,660

(22) Filed: May 1, 2014

(65) Prior Publication Data

US 2015/0030223 A1    Jan. 29, 2015

(51) Int. Cl.
*G06K 9/00* (2006.01)
*G06T 15/08* (2011.01)
(Continued)

(52) U.S. Cl.
CPC ............... *G06T 15/08* (2013.01); *A61B 6/037* (2013.01); *A61B 6/583* (2013.01); *A61B 19/52* (2013.01); *A61N 5/1049* (2013.01); *G01R 33/58* (2013.01); *G06T 7/0016* (2013.01); *A61B 5/055* (2013.01); *A61B 2017/00716* (2013.01); *A61B 2017/00725* (2013.01); *A61N 2005/1052* (2013.01); *A61N 2005/1055* (2013.01); *A61N 2005/1061* (2013.01); *G06T 2207/10072* (2013.01)

(58) Field of Classification Search
None
See application file for complete search history.

(56) References Cited

U.S. PATENT DOCUMENTS 2,737,596 A    3/1956    Haupt et al.
2,876,362 A    3/1959    Foderaro
(Continued)

FOREIGN PATENT DOCUMENTS

DE    10 2005 056 698    11/2008
EP         0060771       9/1982
(Continued)

OTHER PUBLICATIONS

Wang et al, Geometric distortion in clinical MRI systems Part I: evaluation using a 3D phantom, 2004, Elsevier, Magnetic Resonance Imaging 22 (2004) 1211-1221.*
(Continued)

*Primary Examiner* — Jason Heidemann
(74) *Attorney, Agent, or Firm* — Knobbe, Martens, Olson & Bear LLP (57) ABSTRACT

Systems and methods for characterizing spatial distortions in location data determined by an imaging system, for example as employed in imaged guided therapy. A three dimensional phantom is custom formed for a desired imaging space of a given imaging system. The phantom includes a large plurality of control points fixed rigidly in space to a high degree of known accuracy. The phantom is fixed to a stereotactic frame defining a known calibrated reference or zero and imaged. An algorithm customized for the phantom determines the spatial locations of the control points. A comparison is made between the known and the determined spatial locations for at least a subset of the control points. The comparison results in indicia for any determined spatial distortions observed. The raw image data can be manipulated to compensate for any spatial distortion. The control points can have fixed locations known to an accuracy of 100 μm or better. The algorithm can determine an initial estimate for the detected location of a control point accurate to .+−.0.5 pixel or better.

19 Claims, 5 Drawing Sheets

(51) Int. Cl.
*A61B 6/03* (2006.01)
*A61B 6/00* (2006.01)
*A61B 19/00* (2006.01)
*G06T 7/00* (2006.01)
*A61N 5/10* (2006.01)
*G01R 33/58* (2006.01)
*A61B 5/055* (2006.01)
*A61B 17/00* (2006.01)

(56) References Cited

U.S. PATENT DOCUMENTS

| | | |
|---|---|---|
| 3,175,085 A | 3/1965 | Avery |
| 3,604,931 A | 9/1971 | Kastner et al. |
| 3,901,588 A | 8/1975 | Longhenry |
| 4,020,356 A | 4/1977 | Brahme |
| 4,070,611 A | 1/1978 | Ernst |
| 4,112,306 A | 9/1978 | Nunan |
| 4,118,631 A | 10/1978 | Froggatt |
| 4,165,479 A | 8/1979 | Mansfield |
| 4,190,772 A | 2/1980 | Dinwiddie et al. |
| 4,198,565 A | 4/1980 | Ono |
| 4,230,129 A | 10/1980 | LeVeen |
| 4,256,966 A | 3/1981 | Heinz |
| 4,262,204 A | 4/1981 | Mirabella |
| 4,287,425 A | 9/1981 | Elliott, Jr. |
| 4,347,440 A | 8/1982 | Haas |
| 4,362,947 A | 12/1982 | Perraudin et al. |
| 4,378,813 A | 4/1983 | Lovelace et al. |
| 4,392,239 A | 7/1983 | Wilkens |
| 4,400,820 A | 8/1983 | O'Dell et al. |
| 4,497,061 A | 1/1985 | Hounsfield |
| 4,505,267 A | 3/1985 | Inada |
| 4,602,622 A | 7/1986 | Bar et al. |
| 4,624,007 A | 11/1986 | Muranushi |
| 4,731,864 A | 3/1988 | Modla |
| 4,791,934 A | 12/1988 | Brunnett |
| 4,796,613 A | 1/1989 | Heumann et al. |
| 4,843,866 A | 7/1989 | Madsen et al. |
| 4,891,829 A | 1/1990 | Deckman et al. |
| 4,901,339 A | 2/1990 | Heinz et al. |
| 4,907,251 A | 3/1990 | Mork et al. |
| 4,971,060 A | 11/1990 | Schneider et al. |
| 5,005,578 A | 4/1991 | Greer et al. |
| 5,012,506 A | 4/1991 | Span et al. |
| 5,014,290 A | 5/1991 | Moore et al. |
| 5,039,867 A | 8/1991 | Nishihara et al. |
| 5,048,070 A | 9/1991 | Maehama et al. |
| 5,048,071 A | 9/1991 | Van Steenburg |
| 5,049,147 A | 9/1991 | Danon |
| 5,054,048 A | 10/1991 | Wang |
| 5,054,049 A | 10/1991 | Manabe |
| 5,079,426 A | 1/1992 | Antonuk et al. |
| 5,090,047 A | 2/1992 | Angotti et al. |
| 5,094,241 A | 3/1992 | Allen |
| 5,117,829 A | 6/1992 | Miller et al. |
| 5,206,893 A | 4/1993 | Hara |
| 5,230,623 A | 7/1993 | Guthrie et al. |
| 5,240,218 A | 8/1993 | Dye |
| 5,242,455 A | 9/1993 | Skeens et al. |
| 5,269,305 A | 12/1993 | Corol |
| 5,278,886 A | 1/1994 | Kobiki et al. |
| 5,279,309 A | 1/1994 | Taylor et al. |
| 5,281,232 A | 1/1994 | Hamilton et al. |
| 5,285,787 A | 2/1994 | Machida |
| 5,297,037 A | 3/1994 | Ifuku |
| 5,361,765 A | 11/1994 | Herlihy et al. |
| 5,370,117 A | 12/1994 | McLaurin, Jr. |
| 5,370,118 A | 12/1994 | Vij et al. |
| 5,402,463 A | 3/1995 | Umetani et al. |
| 5,485,833 A | 1/1996 | Dietz |
| 5,570,409 A | 10/1996 | Yamaguchi et al. |
| 5,625,663 A | 4/1997 | Swerdloff et al. |
| 5,676,673 A | 10/1997 | Ferre et al. |
| 5,727,554 A | 3/1998 | Kalend et al. |
| 5,754,623 A | 5/1998 | Seki |
| 5,755,725 A | 5/1998 | Druais |
| 5,768,405 A | 6/1998 | Mkram-Ebeid |
| 5,792,147 A | 8/1998 | Evans et al. |
| 5,797,924 A | 8/1998 | Schulte et al. |
| 5,800,352 A | 9/1998 | Ferre et al. |
| 5,825,845 A | 10/1998 | Blair et al. |
| 5,866,912 A | 2/1999 | Slater et al. |
| 5,872,829 A | 2/1999 | Wischmann et al. |
| 5,878,112 A | 3/1999 | Koertge |
| 6,026,315 A | 2/2000 | Lenz et al. |
| 6,104,779 A | 8/2000 | Shepherd et al. |
| 6,118,848 A | 9/2000 | Reiffel |
| 6,144,875 A | 11/2000 | Schweikard et al. |
| 6,180,942 B1 | 1/2001 | Tracy et al. |
| 6,195,409 B1 | 2/2001 | Chang et al. |
| 6,195,578 B1 | 2/2001 | Distler et al. |
| 6,282,261 B1 | 8/2001 | Mazess et al. |
| 6,313,915 B1 | 11/2001 | Yanagisawa et al. |
| 6,325,758 B1 | 12/2001 | Carol et al. |
| 6,405,072 B1 | 6/2002 | Cosman |
| 6,420,711 B2 | 7/2002 | Tümer |
| 6,445,766 B1 | 9/2002 | Whitham |
| 6,460,206 B1 | 10/2002 | Blasche et al. |
| 6,466,813 B1 | 10/2002 | Shukla et al. |
| 6,473,490 B1 | 10/2002 | Siochi |
| 6,693,283 B2 | 2/2004 | Eickhoff et al. |
| 6,694,057 B1 | 2/2004 | Miller et al. |
| 6,725,078 B2 | 4/2004 | Bucholz et al. |
| 6,730,921 B2 | 5/2004 | Kraft |
| 6,754,299 B2 | 6/2004 | Patch |
| 6,774,383 B2 | 8/2004 | Norimine et al. |
| 6,775,404 B1 | 8/2004 | Pagoulatos et al. |
| 6,809,325 B2 | 10/2004 | Dahl et al. |
| 6,839,404 B2 | 1/2005 | Clark et al. |
| 6,906,317 B2 | 6/2005 | Bateman et al. |
| 6,953,943 B2 | 10/2005 | Yanagisawa et al. |
| 7,194,063 B2 | 3/2007 | Dilmanian et al. |
| 7,659,521 B2 | 2/2010 | Pedroni |
| 7,659,528 B2 | 2/2010 | Uematsu |
| 7,695,192 B2 | 4/2010 | Henderson et al. |
| 7,796,730 B2 | 9/2010 | Marash et al. |
| 7,820,989 B2 | 10/2010 | Sommer |
| 7,834,334 B2 | 11/2010 | Grozinger et al. |
| 7,834,336 B2 | 11/2010 | Boeh et al. |
| 7,934,869 B2 | 5/2011 | Ivanov et al. |
| 7,940,894 B2 | 5/2011 | Balakin |
| 8,045,679 B2 | 10/2011 | Balakin |
| 8,049,176 B1 | 11/2011 | Majewski et al. |
| 8,111,806 B2 | 2/2012 | Amelia et al. |
| 8,144,832 B2 | 3/2012 | Balakin |
| 8,189,889 B2 | 5/2012 | Pearlstein et al. |
| 8,223,920 B2 | 7/2012 | Amelia et al. |
| 8,229,072 B2 | 7/2012 | Balakin |
| 8,331,531 B2 | 12/2012 | Fahrig et al. |
| 8,334,509 B2 | 12/2012 | Iseki et al. |
| 8,487,278 B2 | 7/2013 | Balakin |
| 8,519,365 B2 | 8/2013 | Balakin |
| 8,598,543 B2 | 12/2013 | Balakin |
| 8,688,197 B2 | 4/2014 | Balakin |
| 8,737,707 B2 | 5/2014 | Pearlstein et al. |
| 2003/0007601 A1 | 1/2003 | Jaffray et al. |
| 2003/0031301 A1 | 2/2003 | Longton et al. |
| 2003/0095625 A1 | 5/2003 | Steinberg |
| 2003/0155530 A1 | 8/2003 | Adnani et al. |
| 2003/0228260 A1 | 12/2003 | Filler |
| 2004/0034438 A1 | 2/2004 | Uematsu |
| 2004/0042583 A1 | 3/2004 | Wackerle et al. |
| 2004/0184583 A1 | 9/2004 | Nagamine et al. |
| 2005/0054910 A1 | 3/2005 | Tremblay et al. |
| 2005/0085717 A1 | 4/2005 | Shahidi |
| 2005/0139758 A1 | 6/2005 | White et al. |
| 2006/0166353 A1 | 7/2006 | Alfano et al. |
| 2006/0175529 A1 | 8/2006 | Harmon et al. |
| 2007/0009441 A1 | 1/2007 | Erathodiyil et al. |
| 2007/0031337 A1 | 2/2007 | Schulte |
| 2007/0100226 A1* | 5/2007 | Yankelevitz et al. ......... 600/407 |
| 2007/0122020 A1 | 5/2007 | Claus et al. |
| 2008/0071131 A1 | 3/2008 | Rietzel |

(56) References Cited

U.S. PATENT DOCUMENTS

| | | | |
|---|---|---|---|
| 2009/0088620 A1* | 4/2009 | Zagorchev et al. | 600/407 |
| 2009/0154645 A1 | 6/2009 | Lifshitz et al. | |
| 2009/0168960 A1 | 7/2009 | Jongen et al. | |
| 2009/0230315 A1 | 9/2009 | Hunter et al. | |
| 2009/0261275 A1 | 10/2009 | Rietzel | |
| 2009/0274269 A1 | 11/2009 | Foland | |
| 2009/0304153 A1 | 12/2009 | Amelia et al. | |
| 2009/0309046 A1 | 12/2009 | Balakin | |
| 2009/0314960 A1 | 12/2009 | Balakin | |
| 2010/0008468 A1 | 1/2010 | Balakin | |
| 2010/0008469 A1 | 1/2010 | Balakin | |
| 2010/0014639 A1 | 1/2010 | Balakin | |
| 2010/0027745 A1 | 2/2010 | Balakin | |
| 2010/0054414 A1 | 3/2010 | Herrmann | |
| 2011/0006224 A1 | 1/2011 | Maltz et al. | |
| 2011/0047469 A1 | 2/2011 | Baumann et al. | |
| 2011/0049377 A1 | 3/2011 | Morf et al. | |
| 2011/0118588 A1 | 5/2011 | Komblau et al. | |
| 2011/0182806 A1 | 7/2011 | Schulte et al. | |
| 2011/0196223 A1 | 8/2011 | Balakin | |
| 2011/0220794 A1 | 9/2011 | Censor et al. | |
| 2011/0230754 A1 | 9/2011 | Overweg | |
| 2011/0248188 A1 | 10/2011 | Brusasco et al. | |
| 2011/0313232 A1 | 12/2011 | Balakin | |
| 2012/0056109 A1 | 3/2012 | Lomax | |
| 2012/0143051 A1 | 6/2012 | Balakin | |
| 2012/0150018 A1 | 6/2012 | Yamaya et al. | |
| 2012/0165651 A1 | 6/2012 | Inaniwa et al. | |
| 2012/0181428 A1 | 7/2012 | Bert et al. | |
| 2012/0205557 A1 | 8/2012 | Rinecker | |
| 2012/0209109 A1 | 8/2012 | Balakin | |
| 2013/0015352 A1 | 1/2013 | Karonis et al. | |

FOREIGN PATENT DOCUMENTS

| | | |
|---|---|---|
| EP | 0247449 | 12/1987 |
| JP | 1977-007283 A | 8/1977 |
| JP | 53-103671 | 8/1978 |
| JP | 01-209077 | 8/1989 |
| JP | 01-274741 | 10/1989 |
| JP | 04-102465 | 3/1992 |
| JP | 04-339282 | 11/1992 |
| JP | 06-209926 | 9/1994 |
| JP | 07-047079 A | 2/1995 |
| JP | H08-80016 | 3/1996 |
| WO | WO 2010/109586 | 9/2010 |

OTHER PUBLICATIONS

Wang et al, Geometric distortion in clinical MRI systems Part II: correction using a 3D phantom Elsevier, Magnetic Resonance Imaging 22 (2004) 1223-1232.*

Abragram, "The Principles of Nuclear Magnetism" at the Clarendon Press, Oxford, 1978, p. 66.

Baldwin et al., "Characterization, prediction, and correction of geometric distortion in 3 T MR images", Medical Physics, Feb. 2007, vol. 34, No. 2, pp. 388-399.

Dixit et al., "Development of Gas Microstrip Detectors for Digital X-Ray Imaging and Radiation Dosimetry", IEEE Instrumentation and Measurement Technology Conference, May 19-21, 1997, vol. 2, pp. 1357-1360.

Doran, et al., "A Complete Distortion Correction for MR Imagels: I. Gradient Warp Correction.", Phys. Med. Biol., 2005, vol. 50, pp. 1343-1361.

International Search Report and Written Opinion re PCT/US2009/034766, dated Apr. 14, 2009.

International Preliminary Report on Patentability dated Aug. 24, 2010, International Patent Application No. PCT/US2009/034766.

Kittle D. et al., "Technical Note: Rapid prototyping of 3D grid arrays for image guided therapy quality assurance," Am. Assoc. Phys. Med., 2008, vol. 35, Issue 12, pp. 5708-5712.

Laloup, "Cancer Therapy Without Side Effects Nearing Trials," dated Apr. 13, 2008 from http://www.wired.com/print/medtech/health/news/2008/04/kanzius_therapy on Apr. 23, 2008.

Liu et al., "A position-sensitive particle detector with a meander-type delay line", Nuclear Instruments and Methods in Physics Research, vol. A240, 1985, North Holland, Amsterdam, pp. 139-144.

McGurk, et al., "Rapid Prototyping Techniques for Anatomical Modelling in Medicine", Ann R Coll Surg Engl, 1997, vol. 79, Issue 3, pp. 169-174.

Metcalfe et al., "The Physics of Radiotherapy X-Rays and Electrons", Capter 12: Patient Immobilizationa nd Image Guidance, 2007, p. 727-764.

"BrainLAB Radiotherapy Solutions—Product Overview", 2004, BrainLAB AG, in 6 pages.

Pyarali et al., "Design and Performance of an Object-Oriented Framework for High-Speed Electronic Medical Imaging," Computing Systems, Usenix Association, Berkeley, CA US, vol. 9, No. 4, 1996, pp. 331-375.

Ramani et al., "A QA phantom for dynamic stereotactic radiosurgery: quantitative measurements", Med Phys, 1995, vol. 22, Issue 8, pp. 1343-1346.

Schulte et al., "Nanoparticle-Enhanced Proton Computed Tomography: A Monte Carlo Simulation Study", Biomedical Imaging: Nano to Macro, 2004, IEEE International Symposium, Apr. 15-18, 2004, pp. 1354-1356 in 3 pages.

Wang et al., "A novel phantom and method for comprehensive 3-dimensional measurement and correction of geometric distortion in magnetic resonance imaging", Magn Reson Imaging, 2004, vol. 22, Issue 4, pp. 529-542.

Webb, "A Review of Rapid Prototyping (RP) techniques in the medical and biomedical sector", J Med Eng Technol, 2000, vol. 24, Issue 4, pp. 149-153.

Weigel et al., "Design and preparation of polymeric scaffolds for tissue engineering", Expert Rev Med Devices, 2006, vol. 3, Issue 6, pp. 835-851.

Yang et al., "The design of scaffolds for use in tissue engineering. Part II. Rapid Prototyping techniques", Tissue Eng, 2002, vol. 8, Issue 1, pp. 1-11.

Yu et al., "A phantom study of the geometric accuracy of computed tomographic and magnetic resonance imaging stereotactic localization with the Leksell stereotactic system", Neurosurgery, 2001, vol. 48, Issue 5, pp. 1092-1098.

* cited by examiner

SYSTEMS AND METHODS FOR CHARACTERIZING SPATIAL DISTORTION IN 3D IMAGING SYSTEMS

INCORPORATION BY REFERENCE TO ANY PRIORITY APPLICATIONS

Any and all applications for which a foreign or domestic priority claim is made are identified in the Application Data Sheet filed with the present application and are incorporated by reference under 37 CFR 1.57 and made a part of this specification.

BACKGROUND

1. Field

This disclosure relates to the field of image guided therapy and to systems and methods for creating and utilizing phantoms for characterizing imaging errors to facilitate correction of such errors.

2. Description of Related Art

Image Guided Therapies (IGT) refers to a wide range of existing and developing treatment modalities that employ one or more imaging technologies to assist more effective delivery of the related therapy. IGT can include but is not limited to such treatment modalities as image guided surgery, radiosurgery, radiotherapy, and other existing and developing types of therapy. In general, IGT utilizes one or more imaging technologies to gather information indicative of the internal structures and/or condition of tissue of interest. Image data is obtained that is generally manipulated by a computer system and associated applications software to generate and display a three dimensional virtual model or image of the imaged region. The image data can be used to more accurately locate regions of interest in space to facilitate more accurate and focused delivery of therapy to the regions of interest.

In many applications, the safety and efficacy of an IGT being used is dependent on the spatial accuracy of a 3D imaging system. For example, certain IGTs are directed to locating specific treatment regions or volumes and accurately delivering the appropriate therapy to the identified target. Errors in accurately identifying the spatial location of a desired target region can compromise the ability to accurately deliver the appropriate therapy. This can at best compromise the efficacy of the intended therapy by misdirecting the therapy and in some applications can have safety concerns, for example by unintentionally delivering the therapy to non-target regions.

A variety of imaging technologies can be used in IGT, however all known imaging technologies suffer from some degree of spatial distortion. Magnetic Resonance Imaging (MRI) utilizes a powerful magnetic field that is applied to an imaging space to preferentially align nuclear magnetization vectors, generally hydrogen atoms in water present in the tissue. Radio frequency fields are applied to alter the alignment of this magnetization thereby inducing perturbations in the magnetic field that are detectable by the MRI system. However, location data obtained via MRI systems is subject to spatial distortion from magnetic field distortions as well as chemical shifts that may occur within the imaging volume.

Computed Tomography (CT) is another type of imaging technology that utilizes computer processing to generate a virtual three dimensional image object by analyzing a generally large plurality of two dimensional x-ray images taken from different perspectives. However, CT imaging is also subject to distortion from a phenomenon known as beam hardening.

Single photon emission computed tomography (SPECT) and positron emission tomography (PET) are nuclear medicine imaging technologies that utilize radioactive tracer materials and detection of gamma rays to produce three dimensional images, frequently indicative of functional processes in the living body. In general, the tracers selected for use in SPECT systems emit gamma radiation that is detected directly whereas tracers selected for use in PET systems emit positrons which annihilate with electrons generally within a few millimeters inducing two gamma photons to be emitted and subsequently detected. SPECT and PET systems are subject to spatial distortion from such factors as attenuation and/or scatter of the gamma rays or gamma photons.

As previously noted, efficacy and safety of IGT is dependent on the accuracy of the imaging technologies used. It will thus be appreciated that there exists an ongoing need for improved systems and methods of more accurately imaging an image volume. There is also a need for characterizing spatial distortions present in an existing, or yet to be developed, imaging system.

SUMMARY

Embodiments include a method for characterizing spatial distortion of a medical imaging system, the method comprising estimating a contour and dimensions of a desired target volume, determining a desired coordinate system, determining a desired arrangement and spacing of a plurality of control points, wherein the desired arrangement and spacing is matched to the determined contour, dimensions, and coordinate system, fabricating a three dimensional phantom matched to the determined arrangement and spacing of the plurality of control points and configured to define the control points in a substantially rigid structure, fixing the phantom with respect to a stereotactic frame such that the plurality of control points defines a corresponding plurality of first known spatial locations, imaging the phantom, determining second measured spatial locations based on the imaging, comparing at least a selected subset of the first known spatial locations with corresponding second measured spatial locations, and calculating indicia of any indicated spatial distortion between the first known spatial locations and the corresponding second measured spatial locations.

Embodiments include estimating the contour and dimensions of the desired target volume is performed to match a portion of a living body.

Embodiments further include wherein the three dimensional phantom is fabricated at least in part via a rapid prototyping process.

Embodiments further include wherein the rapid prototyping process comprises selective laser sintering.

Embodiments further include operating on the second measured spatial locations so as to create a corrected set of measured spatial locations having reduced spatial distortion with respect to the first known spatial locations.

Embodiments further include fabricating the phantom such that the plurality of control points is distributed in a substantially uniform spacing.

Embodiments include a system for characterizing spatial errors in a medical imaging system, the system comprising a phantom defining a plurality of control points, wherein the control points are distributed in three dimensional space and substantially fixed with respect to each other, a fixture rigidly connectable to the phantom and connectable to a stereotactic frame of a medical imaging system such that the control points can be positioned to occupy first known spatial locations within an imaging space of the imaging system, and an analysis module in communication with the imaging system so as to obtain data indicative of second measured spatial locations of at least a subset of the plurality of control points as determined by the imaging system and wherein the analysis module compares the first known spatial locations with the corresponding second measured spatial locations and calculates an indicia of any determined variation between the first known spatial locations and the corresponding second measured spatial locations for at least the subset of the plurality of control points.

Embodiments further include a chamber configured to enclose the phantom.

Embodiments further include wherein the chamber is configured to enclose the phantom in a substantially fluid tight manner and wherein the chamber is further provided with contrast material.

Embodiments further include wherein the analysis module further operates on the second measured spatial locations so as to create a corrected set of measured spatial locations having reduced spatial distortion with respect to the first known spatial locations.

Embodiments further include wherein the plurality of control points are distributed in a substantially uniform spacing.

Embodiments further include wherein the phantom is custom matched to the imaging system.

Embodiments further include wherein the phantom is custom matched to at least one specific imaging volume of the imaging system.

Embodiments further include storage media provided with machine executable instructions configured to induce a computer system to perform the processes of apply a three dimensional low pass filter to an original image volume resulting from an imaging operation of a three dimensional structure, determine a selected kernel matched to the three dimensional structure, convoluting the filtered image volume with the selected kernel, and locating local maxima for the convoluted image.

Embodiments further include instructions to induce the computer system to perform the process of resampling image intensity curves in multiple dimensions.

Embodiments further include instructions to induce the computer system to perform the process of making a decision whether or not to iterate previously performed processes and, if true, to iterate the processes of convoluting the filtered image volume with the selected kernel, locating local maxima for the convoluted image and resampling image intensity curves in multiple dimensions and, if not true, to perform the process of using a center of gravity of a last set of resampled intensity curves as estimates for a spatial coordinate point.

Embodiments further include instructions to induce the computer system to perform the process of comparing at least a selected subset of first known spatial locations with corresponding located local maxima and calculating indicia of any indicated spatial distortion between the first known spatial locations and the corresponding located local maxima.

Embodiments further include instructions to induce the computer system to perform the process of operating on the located local maxima so as to create a corrected set of located local maxima having reduced spatial distortion with respect to the first known spatial locations.

Embodiments include a method for characterizing spatial distortion of an imaging system, the method comprising estimating a contour and dimensions of a desired target volume, determining a desired coordinate system, determining a desired arrangement and spacing of a plurality of control points, wherein the desired arrangement and spacing is matched to the determined contour, dimensions, and coordinate system, fabricating a three dimensional phantom matched to the determined arrangement and spacing of the plurality of control points and configured to define the control points in a substantially rigid structure, fixing the phantom with respect to a stereotactic frame such that the plurality of control points defines a corresponding plurality of first known spatial locations, imaging the phantom, determining second measured spatial locations based on the imaging, comparing at least a selected subset of the first known spatial locations with corresponding second measured spatial locations, and calculating indicia of any indicated spatial distortion between the first known spatial locations and the corresponding second measured spatial locations.

Embodiments include a system for characterizing spatial errors in an imaging system, the system comprising a phantom defining a plurality of control points, wherein the control points are distributed in three dimensional space and substantially fixed with respect to each other, a fixture rigidly connectable to the phantom and connectable to a stereotactic frame of the imaging system such that the control points can be positioned to occupy first known spatial locations within an imaging space of the imaging system, and an analysis module in communication with the imaging system so as to obtain data indicative of second measured spatial locations of at least a subset of the plurality of control points as determined by the imaging system and wherein the analysis module compares the first known spatial locations with the corresponding second measured spatial locations and calculates an indicia of any determined variation between the first known spatial locations and the corresponding second measured spatial locations for at least the subset of the plurality of control points. These and other objects and advantages will become more apparent from the following description taken in conjunction with the accompanying drawings.

DETAILED DESCRIPTION OF CERTAIN EMBODIMENTS

Figure 1:
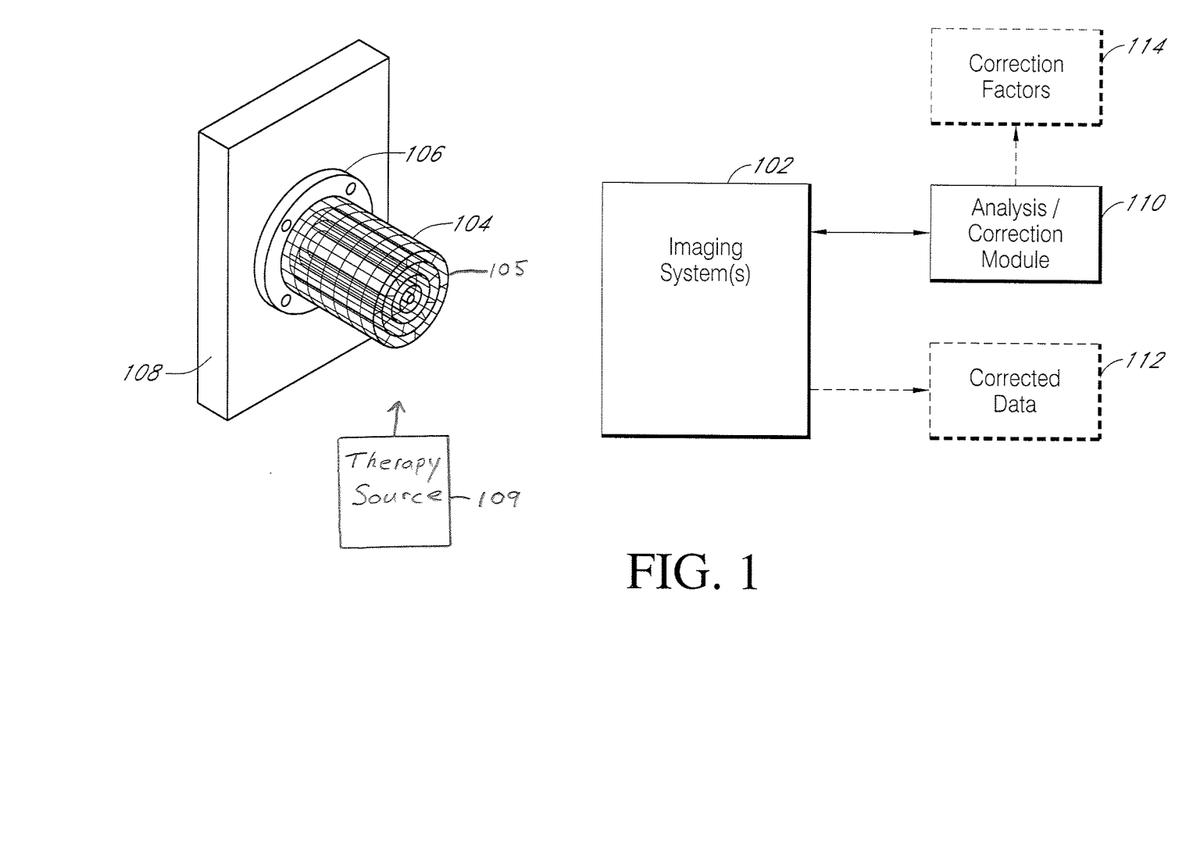
FIG. 1 is a schematic illustration of one embodiment of a system for characterizing spatial distortion errors of an imaging system, for example an imaging system used in image guided therapy.

FIG. 1 illustrates schematically embodiments of a system for characterizing spatial distortions that may occur in image data obtained by an imaging system 102. The imaging system 102 can comprise one or more of a wide variety of imaging technologies including but not limited to MRI, CT, SPECT, and PET. The imaging system 102 can passively monitor one or more types of emissions from an imaging volume or space. The imaging systems 102 may also generate or project fields, energies, and/or particles and monitor interactions of these projected or generated energies and/or particles with the imaged volume.

As previously noted, known imaging systems 102 are subject to at least some degree of spatial distortion. In at least some applications, the spatial distortion is at least in part generally repeatable and can be referred to as machine dependent distortion. Such distortion is generally dependent on the design and construction of a given imaging system 102 and the nature of the imaging modality. In some applications, spatial distortion can also be dependent, at least in part, on the physical characteristics of materials being imaged. In some known imaging systems 102, the spatial distortion can result in discrepancies between the true location of a given point from its measured spatial location as determined by the imaging system 102. The spatial distortion normally varies for individual imaging systems 102, however can commonly range in magnitude from on the order of several millimeters to several centimeters in error. Embodiments described herein facilitate accurate identification or characterization of such errors at a large plurality of control points within an imaging volume and facilitate correction of any distortions or errors to assist more accurate delivery of image guided therapies.

The system comprises a three dimensional or 3D phantom 104. The phantom 104 comprises material that is specifically selected to be distinguished by an associated imaging system 102 from surrounding material. The 3D phantom 104 can comprise a three dimensionally extending grid or frame structure comprising a plurality of interconnected solid elongate members. The connection or intersection of adjoining elongate members defines a plurality of control points 105 which are spatially distributed in three dimensions. Individual elongate members can be considered as posts or struts. The individual elongate members can be substantially straight or can define a curved structure. A combination of substantially straight and of curved members is possible.

In some embodiments, a 3D phantom 104 is formed from hollow elements which can be filled with fluid containing contrast agent or radioactive material that can be readily distinguished by an associated imaging system 102 from surrounding material. The connection or intersection of these fluid columns defines a plurality of control points 105 which are spatially distributed in three dimensions. The individual hollow elongate members can be substantially straight or can define a curved structure. A combination of substantially straight and of curved members is possible.

The 3D phantom 104 is a substantially rigid structure and thus the control points 105 are substantially maintained in a fixed time invariant spatial location with respect to each other. This allows the 3D phantom 104 to maintain a large plurality of control points 105 distributed in three dimensions and having a spatial location knowable to within a high degree of accuracy. In some embodiments, the spatial location of a given control point 105 is known accurate to within approximately 0.1 mm or 100 μm or better. In some embodiments, the 3D phantom 104 maintains the control points 105 to within a known accuracy of 0.06 mm or 60 μm or better. In general, a higher degree of known spatial location accuracy is preferable, however various levels of accuracy can be indicated, based on speed and cost concerns and the accuracy requirements for a given IGT.

Figure 3:
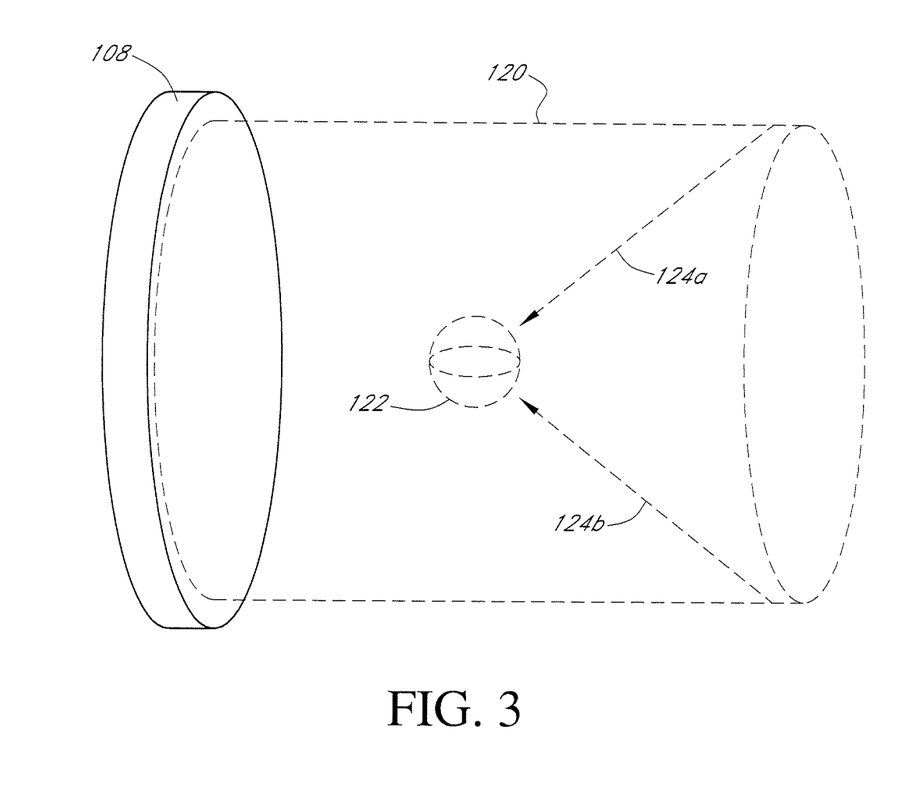
FIG. 3 is a detailed schematic illustration of an embodiment of an imaging space or volume, for example in an image guided therapy system including a desired target region or volume and a plurality of treatment paths.

In some embodiments, a 3D phantom 104 is formed to correspond generally to the contours and dimensions of a desired image space or volume 120 (see FIG. 3). The image space or volume 120 corresponds generally to a volume of space from which the imaging system 102 will obtain measurements and create a virtual image from. In many applications, the image space or volume 120 will be fixed with respect to a stereotactic frame 108. The configuration and size of a 3D phantom 104 can be matched to the image space or volume 120 of interest.

In some embodiments, a 3D phantom 104 can comprise a three dimensionally extending grid that is formed around an incorporated internal volume that models or replicates anatomical structures and/or implants known to produce subject dependent imaging distortions. For example, sinuses containing air can create distortions in MR based imaging of the brain. By assessing distortion due to anatomical structures and/or implants, significant improvements in the accuracy of image guided treatments can be provided for individual patients.

For example, image guided therapy is frequently utilized for localized treatment of a particular portion of the living body, for example a region of interest within a patient's head. Accordingly, in at least some applications, an imaging system 102 need not and may not develop image data of the entire living body. Accordingly, the 3D phantom 104 can be configured and sized to correspond generally to the region of interest. While FIG. 1 illustrates an embodiment of 3D phantom 104 having a generally cylindrical contour or shape, this is simply illustrative of one embodiment. In other embodiments, a 3D phantom 104 can have other shapes or contours including but not limited to spheres, cubes, rectangular prisms, triangular prisms, and other geometric shapes. In yet other embodiments, the 3D phantom 104 can describe irregular geometries, for example an anthropomorphic contour. Other shapes and contours are possible.

In various embodiments, a given imaging system 102 may employ or be capable of employing one or multiple coordinate systems in developing the virtual image generated by the imaging system 102. For example, a given imaging system 102 may employ Cartesian coordinates, spherical or polar coordinates, and/or cylindrical coordinates. Accordingly, in at least some applications, the 3D phantom 104 is preferably constructed such that the control points 105 are spatially oriented and matched in such a manner as to cooperate with the particular coordinate system(s) used by an associated imaging system 102. Thus, in various embodiments, the 3D phantom 104 can have the control points 105 positioned generally along orthogonal or Cartesian axes, polar or spherical axes, or cylindrical axes.

Depending on the needs of a given application, the individual control points 105 can be generally uniformly distributed within the 3D phantom 104 or can be distributed in a wide variety of non-uniform distributions. In one non-limiting embodiment, a 3D phantom 104 comprises a plurality of control points 105 arranged in a substantially uniform distribution and having a point to point spacing for the control points 105 of approximately 8 mm. This embodiment can comprise a 3D phantom 104 formed of polyamide. Such an embodiment has been found particularly effective in characterizing spatial distortions in imaging systems 102 comprising MRI technologies.

As previously noted, an imaging system 102 is frequently utilized in combination with a stereotactic frame 108. The stereotactic frame 108 generally maintains a substantially fixed rigid spatial reference or origin that can be maintained during both an imaging process and a treatment process. For example, in some embodiments a stereotactic frame 108 can comprise a stereotactic halo configured to maintain a patient's head in a relatively fixed immobile location. In one embodiment, a fixture 106 is included that can be rigidly connected to the phantom 104 and to the stereotactic frame 108. In some embodiments, connection of the fixture 106 to the phantom 104 is substantially permanent and in other embodiments the connection can be removable or detachable. In at least some applications, it will be generally preferred that the rigid connection between the fixture 106 and the stereotactic frame 108 be removable. This aspect provides the advantage of rigidly fixing the 3D phantom 104 with respect to the stereotactic frame 108, however in a temporary or removable manner. This facilitates utilization of the same stereotactic frame 108 for imaging the 3D phantom 104 as well as for delivery of therapy, such as from a therapy source 109.

As previously noted, a given imaging system 102 is generally subject to at least some degree of spatial distortion when developing image data from an image space or volume 120. By imaging one or more embodiments of 3D phantom 104, the imaging system 102 can develop measured location data, for example of the plurality of control points 105. This measured location data can be compared with the known location of the control points 105, as the 3D phantom 104 comprises a substantially rigid structure which is rigidly connected to a stereotactic frame 108 defining a known spatial reference or zero.

Figure 2:
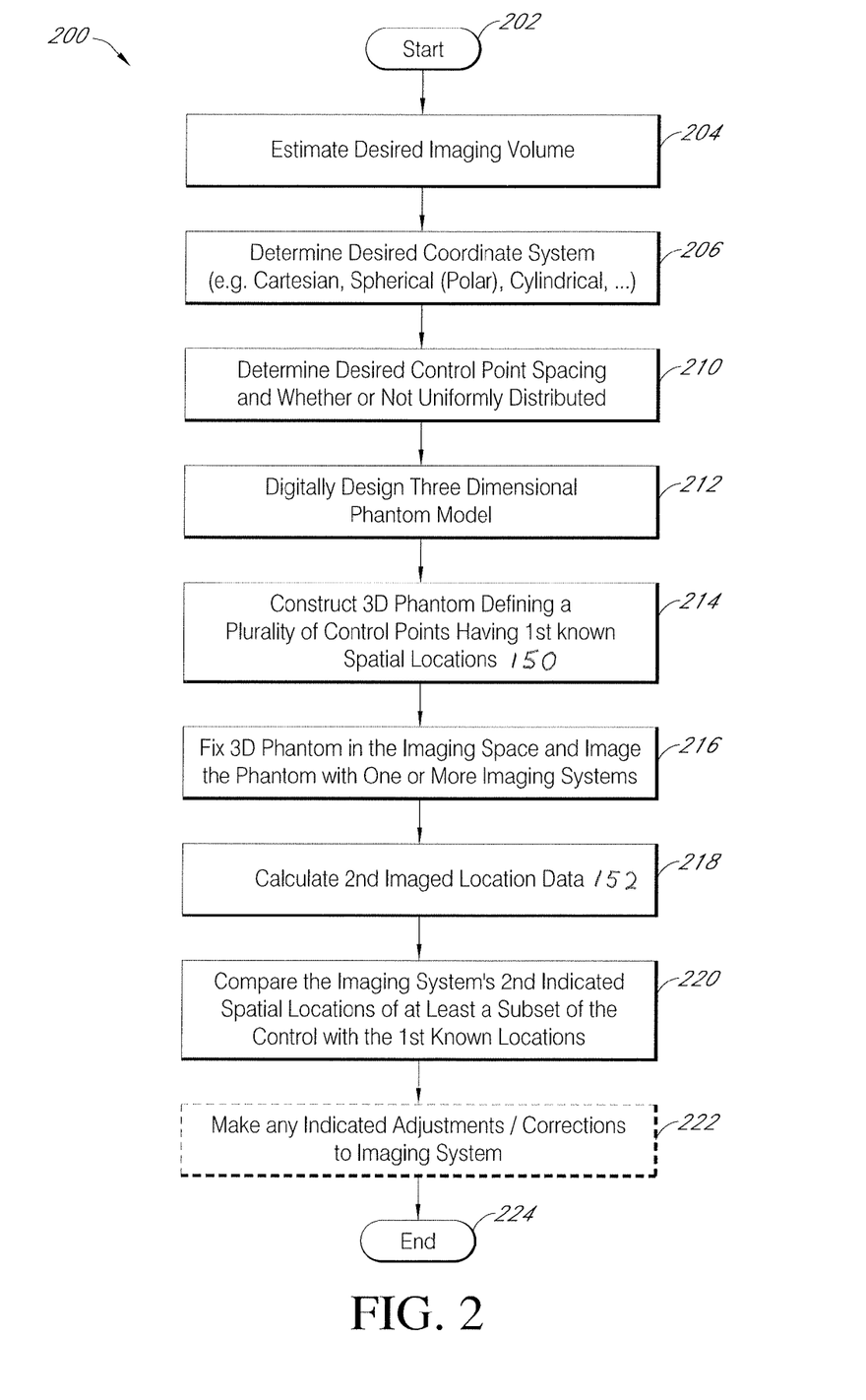
FIG. 2 is a flow chart of embodiments of characterizing spatial distortion in an imaging system.

In one embodiment, image data obtained by an imaging system 102 can be communicated to an analysis module 110. The analysis module 110 can comprise machine executable code stored on computer readable storage media, wherein the code is configured to induce a computer system to perform the actions described for one or more of the embodiments described herein. The analysis module 110 can be provided with the known location data of the plurality of control points 105 of the 3D phantom 104. Thus, the known location of a given control point 105 can comprise a first known spatial location 150 (FIG. 2). The measured spatial location of the same control point 105 as determined by the imaging system 102 can comprise a second measured or imaged spatial location 152 (FIG. 2). The analysis module 110 can be configured to compare the first known spatial location 150 with the second measured spatial location 152 for each of a plurality of control points 105 and use this comparison to characterize any spatial distortion indicated by the comparison.

By employing computer processing and associated applications software and memory, the analysis module 110 can rapidly characterize any spatial distortion between the first and second spatial locations 150, 152 for a large plurality of control points 105 distributed within an image space 120. Depending on the requirements of a given application, the analysis module 110 can analyze all or substantially all of the control points 105 comprising the 3D phantom 104. In some applications, the analysis module 110 may analyze only a selected subset of the total plurality of control points 105. It will be understood that the particular boundaries/parameters of a selected subset of the control points 105 can be selected based on the needs and requirements of a particular application.

In some embodiments, communication between the imaging system 102 and analysis module 110 is bidirectional. In such embodiments, the analysis module 110 can be further configured to provide correction information to accommodate and correct for any identified spatial distortions. Thus, in some embodiments, an analysis/correction module 110 can obtain image data from the imaging system 102, analyze this data for any indicated spatial distortions, and provide return data and/or commands to the imaging system 102. Thus, in some embodiments, the imaging system 102 can provide corrected data 112 in cooperation with an analysis/correction module 110.

It will be understood that in some embodiments, an analysis/correction module 110 can be physically integrated with the imaging system 102. In some embodiments, an analysis/correction module 110 can be materially separate but in communication with an imaging system 102. It will be further understood that the operation of the analysis/correction module 110 need not be concurrent with generation of or communication of image data from the imaging system 102. Thus, the analysis and correction processes performed by various embodiments as described herein can be performed offline with respect to operation of the imaging system 102 or can occur at least in part concurrently therewith. In some embodiments, analysis of any spatial distortions occurs substantially concurrently or in parallel with generation of the image data.

In some embodiments, communication between an imaging system 102 and an analysis/correction module 110 can be unidirectional from the imaging system 102 to the analysis/correction module 110. Thus, in some embodiments, the corrected data 112 can be obtained from the analysis/correction module 110 but not necessarily provided to the imaging system 102 itself. Thus, the corrected data 112 can be provided for use by a clinician or other user while the imaging system 102 provides only "raw data" or data including the spatial distortion.

In yet other embodiments, an analysis module 110 may provide only analysis of any spatial distortions present in a given imaging system 102. For example, in some embodiments, an analysis module 110 can generate and communicate correction factors 114 indicative of the magnitude and direction of any discrepancies between the first known spatial location 150 and second measured or imaged spatial location 152 of one or more control points 105. The correction factors 114 can be utilized by a clinician or other users or other computer based systems based on the needs of a given application. Thus, in at least some embodiments, neither an imaging system 102 nor an analysis module 110 need necessarily provide final corrected image data 112 of the image space 120.

FIG. 2 illustrates a flow chart of embodiments of methods of characterizing spatial distortion in an imaging system. The method 200 begins in a start block 202 which generally describes installation and initial calibration of the imaging system 102 and the stereotactic frame 108. The start block 202 can include calibration or orientation of the stereotactic frame 108 so as to accurately define a spatial reference or zero.

In a block 204, a desired imaging volume 120 is estimated. Block 204 can include establishing the general contour and dimensions of the desired imaging volume 120. In a block 206, the desired coordinate system is determined. The determination of the desired coordinate system in block 206 is frequently dependent on the characteristics and design of the associated imaging system 102. In many applications, Cartesian coordinates are widely used and understood by clinicians and other users, however spherical and cylindrical coordinate systems can also be used.

In a block 210, a determination is made of the desired control point spacing. A desired spacing between individual control points 105 can vary based on the imaging technology of an associated imaging system 102 as well as the particular operating parameters thereof. Desirable control points 105 spacing can also vary depending on the material characteristics of the patient tissue to be subsequently imaged. Block 210 also includes a determination of whether or not the control points 105 are desirably spaced substantially uniformly or non-uniformly. For example, in some applications, an image space 120 defined by the imaging system 102 may be substantially larger than an actual region or volume of interest, for example a treatment volume or region 122 (FIG. 3). Thus, in at least some applications, it can be more efficient and timely to distribute control points 105 in a non-uniform manner. For example, control points 105 may be more closely spaced in a portion of an overall image space 120 to obtain more accurate characterization of spatial distortions within a smaller region of interest 122 within a larger image space 120. This can simplify construction of a 3D phantom 104 and reduce processing overhead required to characterize the spatial distortion in regions of less interest.

In a block 212, a three dimensional model of the 3D phantom 104 is created. Block 212 can include use of digital design tools such as computed aided design (CAD)/computer aided manufacturing (CAM).

In a block 212, the 3D phantom 104 is constructed based on the three dimensional model developed in block 212 so as to define the selected plurality of control points 105 having first known spatial locations and relationships. In one embodiment, block 214 employs one or more rapid prototyping technologies, for example selective laser sintering (SLS).

In one embodiment, block 214 employs an additive manufacturing technique utilizing a high power laser to selectively fuse relatively small particles or powders of polyamide plastic in a spatially highly accurately controlled manner. In one embodiment, block 214 selectively fuses powdered polyamide by sequentially scanning cross-sections of a bed of powdered polyamide according to the contours and dimensions of the 3D phantom model developed in block 212. As each cross-section is scanned, the powder polyamide fuses to form a layer or level of the 3D phantom 104. Additional polyamide powder can be added with each scanning cross-section and the 3D phantom 104 is constructed in a bottom-up or end-to-end manner.

The combination of a selective laser sintering process based on the accurate three dimensional model developed in block 212 results in a 3D phantom 104 having highly accurate placement of a large plurality of control points 105. As previously noted, in some embodiments the control points 105 are located with an accuracy of 100 μm or more. In some embodiments, the control points 105 are located with an accuracy of 60 μm or less. In other embodiments, other rapid prototyping technologies including but not limited to fused deposition modeling (FDM) and/or serial lithography (SLA) can be utilized. It will be further understood that the 3D phantom 104 comprising polyamide is simply one, non limiting example and other embodiments can employ other materials in addition to or as an alternative to the previously described polyamide, depending on the needs of a given application.

In a block 216, the 3D phantom 104 is fixed in the imaging space 120, for example via attachment of the fixture 106 to the 3D phantom 104 and the stereotactic frame 108. Since the stereotactic frame 108 defines a known and calibrated spatial reference or zero and since the relative locations of the control points 105 are also fixed and known, the true spatial locations of each individual control point 105 is known to a high degree of accuracy. Block 216 also includes imaging the 3D phantom 104 with one or more imaging systems 102 to obtain the second measured or imaged location data 152.

Figure 5:
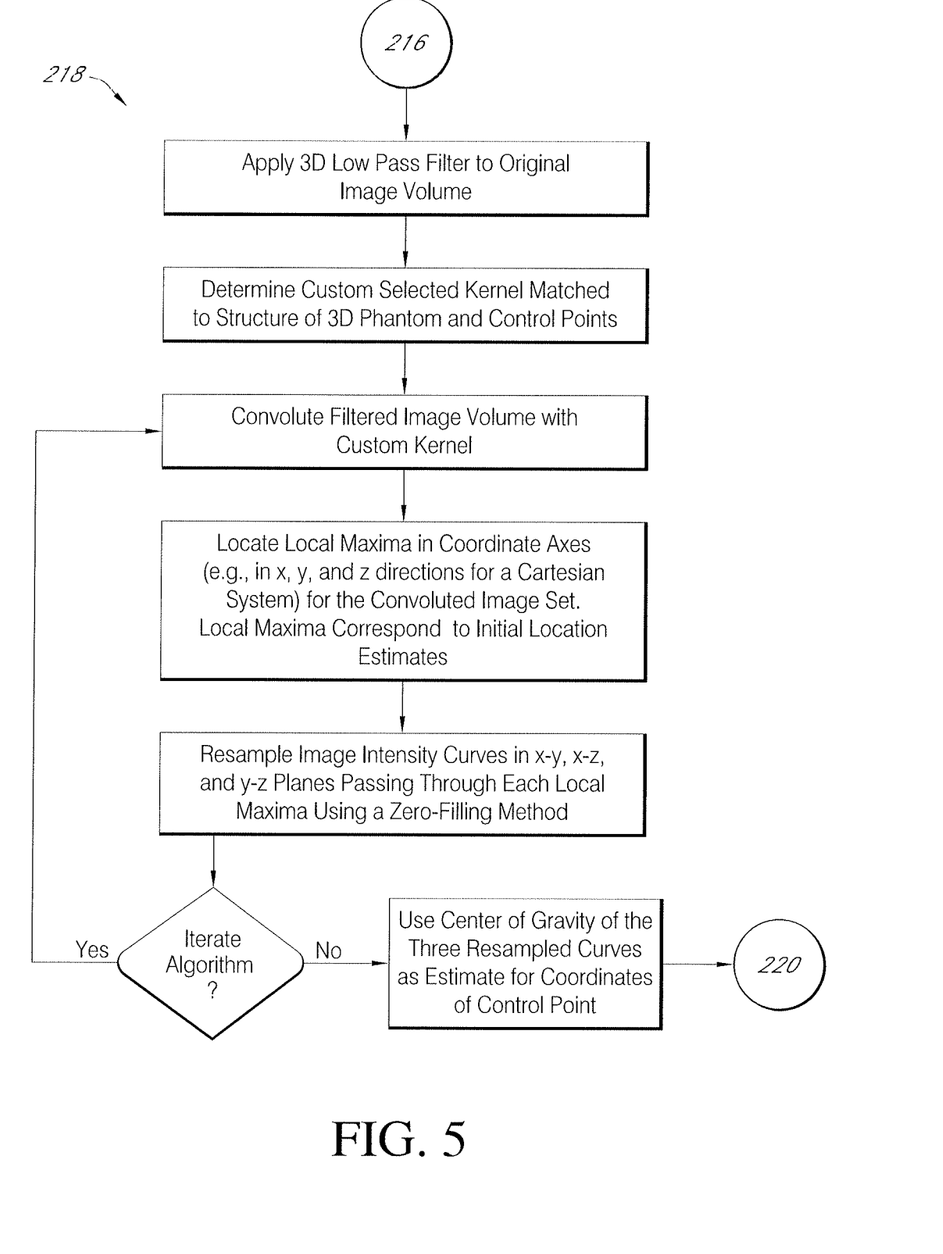
FIG. 5 is a flow chart of embodiments of a computer implemented algorithm for identifying spatial locations of control points in an image space.

In a block 218 a computer implemented algorithm is employed for automated detection of phantom control points 105 in the image space 120. As previously noted, an apparatus employing embodiments of the method 200 can comprise machine executable code stored on computer readable storage media and configured to induce the computer to perform the processes described herein.

In block 218, a 3D low pass filter is applied to the original image volume. A convolution kernel is determined and used that is specifically designed to match the structure of the grid intersections that form the control points 105. The convolution kernel is thus customized for a each phantom 104 geometry and size. For embodiments comprising rectangular grid arrays formed by rectilinearly arranged posts and struts, the kernel preferably used has the general shape of a three-dimensional plus sign. Other kernels can be selected and used for other configurations of the control points 105. The purpose of the convolution is to increase the intensity of the pixels in the intersection points of the image. The intersections after the convolution are about fifty percent brighter than the surrounding grid.

Local maxima of the control points 105 are then found for the convolved image set in the x, y, and z directions. Finding these maxima provides an initial estimate for coordinates of the grid intersections, e.g. the spatial location of the respective control points 105, to an accuracy of .±.0.5 pixel or greater. To refine the estimate, the image intensity curves in the x-y, x-z, and y-z planes passing through each local maximum are resampled using a zero-filling method. The center of gravity for the three resampled curves is used as a new estimate for the coordinates of the grid intersection.

The accuracy of these embodiments for identifying the measured second coordinates for the plurality of control points 105 has been experimentally determined by comparing distances derived from the embodiments of automated detection routine described herein with measurements obtained using a high accuracy caliper. The degree of accuracy obtained was an unexpected positive result.

In a block 220, a comparison is made between the imaging system's second indicated or measured spatial locations with the first known spatial locations of at least a subset of the control points 105. Block 220 can return a magnitude and direction of any detected distortion resolved into each of three dimensions in the appropriate coordinate system. Block 220 can also return a magnitude and direction of any detected distortion as a distortion vector in the appropriate coordinate system. Block 220 can return results as a plurality of individual spatial distortion indicia. Block 220 can also return results as one or more composite or generalized distortion indicia for a plurality of individual spatial distortions.

In a block 222, any indicated adjustments or corrections can be made to the raw image data from the image system 102 to result in corrected or normalized image data 112. As previously noted, this correction of block 222 can be performed by an analysis/correction module 110, by the imaging system 102, or by a separate component or process. Due to the large plurality of control points 105 and corresponding large amount of possible spatial distortion data, it is generally strongly preferred that the calculations and corrections described herein be performed via a computer implemented process.

FIG. 3 illustrates schematically one embodiment of an image space or volume 120 in greater detail. As previously described, a stereotactic frame 108 defines a spatial reference or zero for location measurements made in the image space 120. In this embodiment, a subset or smaller region 122 within the image space 120 is of increased interest to the user. In one embodiment, the subset or smaller region corresponds to a treatment space 122 forming a subset or smaller region of the larger overall image space 120. The treatment space 122 can spatially correspond to a future target location for any of a variety of treatment modalities from the treatment source 109. Treatment can include one or more of accelerated proton therapy, ionizing radiation, infrared radiation, laser, and the like. FIG. 3 also illustrates a first and second treatment path 124a, 124b intersecting the treatment space 122 and indicating schematically deliver of the therapy via different spatial approaches. Thus, embodiments can provide characterization of spatial distortion not only of a treatment space or volume 122 of interest within the image space 120, but also one or more treatment paths 124 traversing the image space 120.

Figure 4:
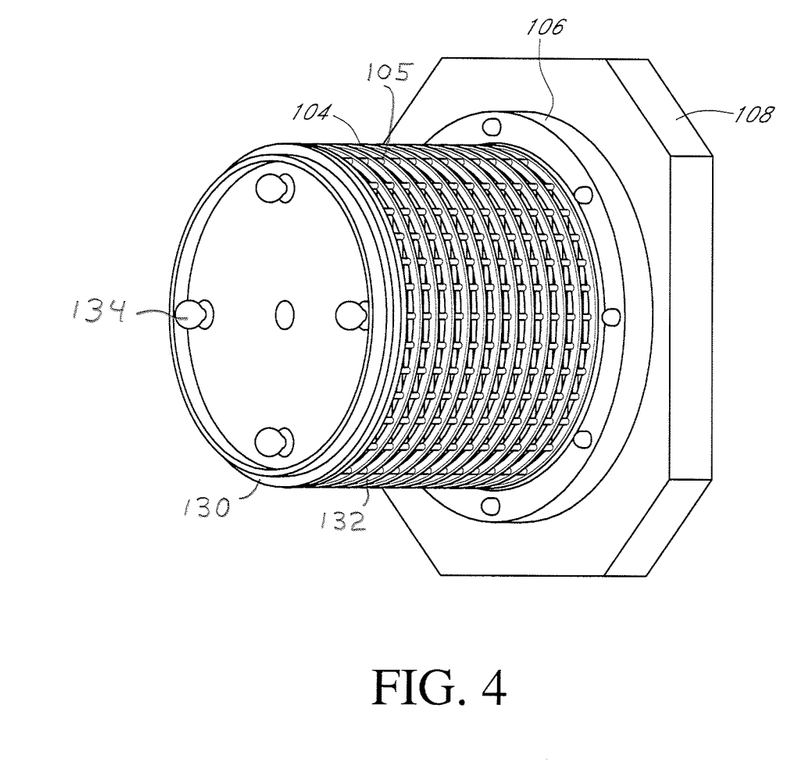
FIG. 4 is a perspective illustration of one embodiment of a high density grid phantom fixed in a stereotactic frame.

FIG. 4 illustrates in greater detail one embodiment of a 3D phantom 104 rigidly attached to a fixture 106 and thus to a fixed stereotactic frame 108. In some embodiments, materials comprising the phantom 104 can be invisible to at least some implementations of imaging system 102. For example, polyamide material is generally invisible to MRI, SPECT, and PET based imaging systems 102.

Thus, one embodiment further comprises a chamber 130 configured to enclose the phantom 104. The chamber 130 shown transparent in FIG. 4 to facilitate viewing of the phantom 104, however is configured to enclose the phantom 104 in a fluid tight manner. The chamber 130 is preferably filled with a contrast material 132 that is visible to the image system 102. The contrast material 132 can comprise copper sulfate solution or mineral oil for MRI based imaging systems 102. The contrast material 132 can comprise gamma or positron emitting substance for SPECT or PET based imaging systems 102. The contrast material 132 allows the imaging system 102 to "see" the boundaries of the phantom 104 and the visible contrast material 132 and thereby identify the location of the control points 105 in the image space 120.

In one embodiment the chamber 130 further comprises one or more access ports 134. The access ports 134 provide access for introducing the contrast material 132. The access ports also facilitate clearing trapped air/bubbles from the chamber 130. The access ports 134 also provide access to the phantom 104 when it is desired to verify the location of the grid control points 105 with respect to the stereotactic frame 108.

For example, in frame-based image guided treatments (which are the most accurate form of image guided therapy), both image and treatment spaces are referenced to the stereotactic frame 108. It can be preferred to express the location of the any spatial distortions identified with the phantom 104 in reference to this same stereotactic frame 108. In practice, once the phantom 104 is placed in the chamber 130, the chamber 130 is securely attached to the stereotactic frame 108. The system can access a metrology lab to precisely measure the grid position of the control points 105 with respect to the stereotactic frame 108 fiducials. The fiducials can vary for a specific implementation of stereotactic frame 108, however can be considered as a coordinate system for the stereotactic frame 108.

Suitable materials and processing methods to form the 3D phantom 104 with the degree of spatial accuracy obtainable according to the embodiments described herein has not previously been available. Appropriate algorithms to analyze the resulting large amount of data obtained against a corresponding large amount of reference data have also not been available. The problems of spatial distortion have existed, but a suitable solution has previously proven elusive. Previous attempts have been incapable of providing the degree of precision and specificity for a given application as the disclosed embodiments. While reference has been made to imaging systems 102 in the context of image guided therapy, it will be understood that embodiments described and illustrated herein can be advantageously employed in any of a wide variety of imaging systems.

Although certain embodiments of the present disclosure have shown, described and pointed out certain novel features as applied to those embodiments, it will be understood that various omissions, substitutions and changes in the form of the detail of the device illustrated may be made by those skilled in the art without departing from the spirit of the invention. Consequently, the scope of the invention should not be limited to the foregoing description but is to be defined by the appended claims.

The following is claimed:

1. A method for characterizing spatial distortion of a medical imaging system, the method comprising:
    estimating a contour and dimensions of a desired target volume;
    determining a desired coordinate system;
    determining a volumetric arrangement and uniform spacing of a plurality of control points in a three-dimensional space, wherein the desired arrangement and spacing is matched to the contour, dimensions, and coordinate system such that the control points are interspersed within and throughout the entire target volume;
    providing a substantially rigid three-dimensional phantom that is matched to the determined volumetric arrangement and uniform spacing of the plurality of control points in the three-dimensional space and that is also configured to rigidly fix the control points in an interspersed manner throughout its substantially rigid structure;
    fixing the phantom with respect to a stereotactic frame such that the plurality of control points defines a corresponding plurality of first known spatial locations;
    imaging the phantom;
    determining second measured spatial locations based on the imaging;
    comparing at least a selected volumetric subset of the first known spatial locations with corresponding second measured spatial locations; and
    calculating indicia of any indicated volumetric spatial distortion between the first known spatial locations and the corresponding second measured spatial locations.

2. The method of claim 1, wherein the estimating the contour and dimensions of the desired target volume is performed to match a portion of a living body.

3. The method of claim 1, wherein the three dimensional phantom is fabricated at least in part via a rapid prototyping process.

4. The method of claim 3, wherein the rapid prototyping process comprises selective laser sintering.

5. The method of claim 1, further comprising operating on the second measured spatial locations so as to create a corrected set of measured spatial locations having reduced spatial distortion with respect to the first known spatial locations.

6. A system for characterizing spatial errors in a medical imaging system, the system comprising:
    a substantially rigid three-dimensional phantom having a plurality of control points, wherein the control points are interspersed uniformly within and throughout a three-dimensional volume and are substantially rigidly fixed with respect to each other;
    a fixture rigidly connectable to the phantom and connectable to a stereotactic frame of a medical imaging system such that the control points can be positioned to occupy first known spatial locations within an imaging space of the imaging system; and
    an analysis module in communication with the imaging system so as to obtain data indicative of second measured spatial locations of at least a volumetric subset of the plurality of control points as determined by the imaging system and wherein the analysis module compares the first known spatial locations with the corresponding second measured spatial locations and calculates an indicia of any determined variation between the first known spatial locations and the corresponding second measured spatial locations for at least the volumetric subset of the plurality of control points.

7. The system of claim 6, further comprising a chamber configured to enclose the phantom.

8. The system of claim 7, wherein the chamber is configured to enclose the phantom in a substantially fluid tight manner and wherein the chamber is further provided with contrast material.

9. The system of claim 6, wherein the analysis module further operates on the second measured spatial locations so as to create a corrected set of measured spatial locations having reduced spatial distortion with respect to the first known spatial locations.

10. The system of claim 6, wherein the plurality of control points are distributed in a substantially uniform spacing within a sub-volume of the phantom corresponding to a planned treatment volume.

11. The system of claim 6, wherein the phantom is custom matched to the imaging system.

12. The system of claim 11, wherein the phantom is custom matched to at least one specific imaging volume of the imaging system.

13. An apparatus for characterizing volumetric spatial distortion of a medical imaging system, the apparatus comprising:
a substantially rigid volumetric phantom comprising:
a three-dimensional volume;
an outer perimeter generally enclosing the three-dimensional volume;
a plurality of control points that are interspersed uniformly within the outer perimeter and throughout the three-dimensional volume and that are substantially rigidly fixed with respect to each other and with respect to the outer perimeter;
a fixture configured to rigidly fix the phantom to a spatial reference point such that the control points occupy known spatial locations within an imaging space of the imaging system; and
an analysis module configured to:
communicate with the imaging system to obtain measured spatial locations of at least a volumetric subset of the plurality of control points as determined by the imaging system;
compare the known spatial locations with the corresponding measured spatial locations as determined by the imaging system; and
calculate any determined variation between the known spatial locations and the corresponding measured spatial locations for at least the volumetric subset of the plurality of control points.

14. The apparatus of claim 13, further configured to use indicia of the determined variation to apply a correction factor, thereby correcting for volumetric spatial distortion of the imaging system.

15. The apparatus of claim 13, wherein the plurality of control points comprise intersections of elongate rigid material.

16. The apparatus of claim 13, wherein the three-dimensional volume has numerous control points volumetrically spaced and thereby configured to be imaged from any of a plurality of angles, the angles corresponding to treatment angles.

17. The apparatus of claim 16, wherein the control points are spaced and configured to allow for effective calibration of a proton beam therapy system having high resolution treatment capabilities.

18. The apparatus of claim 13, wherein the outer perimeter is generally cylindrical, the control points are interspersed in bands exhibiting cylindrical symmetry, and bands of successively wider radius have control points that are spaced farther from each other than in the previous band.

19. The apparatus of claim 13, wherein the control points have one point to point spacing in a target subvolume and a different point to point spacing outside the target subvolume but still within the three-dimensional volume and the outer perimeter thereof.

* * * * *